US007714108B2

(12) United States Patent
Li et al.

(10) Patent No.: US 7,714,108 B2
(45) Date of Patent: May 11, 2010

(54) MAMMALIAN TUMOR SUSCEPTIBILITY GENE PRODUCTS AND THEIR USES

(75) Inventors: Limin Li, Rockville, MD (US); Stanley N. Cohen, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 513 days.

(21) Appl. No.: 10/053,975

(22) Filed: Jan. 18, 2002

(65) Prior Publication Data

US 2003/0138839 A1 Jul. 24, 2003

Related U.S. Application Data

(60) Provisional application No. 60/262,763, filed on Jan. 19, 2001.

(51) Int. Cl.
*C07K 16/00* (2006.01)
*A61K 39/395* (2006.01)

(52) U.S. Cl. .................. 530/387.1; 424/130.1

(58) Field of Classification Search .............. 530/387.1, 530/388.1, 387.9, 87.9
See application file for complete search history.

(56) References Cited

U.S. PATENT DOCUMENTS 5,891,668 A * 4/1999 Li et al. ...................... 435/69.1
5,892,016 A * 4/1999 Brie et al. ................... 536/23.5
6,835,816 B2 * 12/2004 Cohen et al. ............. 530/387.1

FOREIGN PATENT DOCUMENTS

WO  WO 97/18333  5/1997

OTHER PUBLICATIONS

Pornillos et al. (The EMBO Journal 2002; 21: 2397-2406).*
Ferrer et al. (Oncogene 1999; 18: 2253-2259).*
Freshney (Culture of Animal Cells, A Manual of Basic Technique, Alan R. Liss, Inc., 1983, New York, p. 4).*
Dermer (Bio/Technology, 1994, 12:320).*
Jain (Scientific American Jul. 1994).*
Weiner (Seminars Oncology, vol. 26, No. 4, 1999, pp. 41-50).*
Gura (Science, v278, 1997, pp. 1041-1042).*
Dillman (Annals of Internal Medicine, vol. 111, pp. 592-603, 1989).*
Hoffman, et al., "Noncanonical *MMS2*-Encoded Ubiquitin-Conjugating Enzyme Functions in Assembly of Novel Polyubiquitin Chains for DNA Repair", Cell, vol. 96, No. 5, pp. 645-653, 1999.
Li, et al., "The *TSG101* Tumor Susceptibility Gene Is Located in Chromosome 11 Band p15 and Is Mutated in Human Breast Cancer", Cell, vol. 88, No. 1, pp. 143-154, 1997.
Sancho, et al., "Role of UEV-1, an Inactive Variant of the E2 Ubiquitin-Conjugating Enzymes, in In Vitro Differentiation and Cell Cycle Behavior of HT-29-M6 Intestinal Mucosecretory Cells", Molecular and Cellular Biology, vol. 8, No. 1, pp. 576-589, 1998.
Li, et al., "A TSG101/MDM2 regulatory loop modulates MDM2 degradation and MDM2/p53 feedback control", Proc. Natl. Acad. Sci. USA, vol. 98, No. 4, pp. 1619-1624, 2001.
Pomillos, et al., "Structure and functional interactions of Tsg101 UEV domain", EMBO Journal, vol. 21, No. 10, pp. 2397-2406, 2002.
Baker, et al. "*Suppression of human colorectal carcinoma cell growth by wild-type p53*", Science vol. 249: 912-915 (1990).
Buschmann, et al. "*SUMO-1 modification of Mdm2 prevents its self-ubiquitination and increases Mdm2 ability to ubiquitinate p53*", Cell vol. 101: 753-762 (2000).
Chen, et al. "*Mapping of the p53 and mdm-2 interaction domains*", Molecular and Cellular Biology vol. 13(7): 4107-4114 (1993).
Fang, et al. "*Mdm2 is a RING finger-dependent ubiquitin protein ligase for itself and p53*", J. Biol. Chem. vol. 275(12): 8945-8951 (2000).
Feng, et al. "*TSG101 protein steady-state level is regulated post-translationaliy by an evolutionarily conserved COOH-terminal sequence*", Cancer Research vol. 60: 1736-1741 (2000).
Fiddler, et al. "*Amplification of MDM2 inhibits MyoD-mediated myogenesis*", Molecular and Cellular Biology vol. 16(9): 5048-5057 (1996).
Freedman, et al. "*Regulation of the p53 protein by the MDM2 oncoprotein—Thirty-eight G.H.A. Clowes memorial award lecture*", Cancer Research vol. 59: 1-7 (1999).
Gayther, et al. "*Aberrant splicing of the TSG101 and FHIT genes occurs frequently in multiple malignancies and in normal tissues and mimics alterations previously described in tumours*", Oncogene vol. 15: 2119-2126 (1997).
Haupt, et al. "*Mdm2 promotes the rapid degradation of p53*", Nature vol. 387: 296-299 (1997).
Hittlelmann, et al. "Differential regulation of glucocorticoid receptor transcriptional activation via AF-1-associated proteins", The EMBO J. vol. 18(19): 5380-5388 (1999).
Hochstrasser. "*All in the ubiquitin family*", Science vol. 289: 563-564 (2000).
Honda, et al. "Association of p19$^{ARF}$ with Mdm2 inhibits ubiquitin ligase activity of Mdm2 for tumor suppressor p53", The EMBO J. vol. 18(1): 22-27 (1999).
Hsieh, et al. "*RB regulates the stability and the apoptotic function of p53 via MDM2*", Mol. Cell vol. 3: 181-193 (1999).
Jones, et al. "*Rescue of embryonic lethality in Mdm2-deficient mice by absence of p53*", Nature vol. 378: 206-208 (1995).

(Continued)

*Primary Examiner*—Christopher H Yaen
(74) *Attorney, Agent, or Firm*—Steven B. Kelber; Berenato & White

(57) ABSTRACT

The present invention provides methods and compositions for regulating ubiquitination in a cell. In particular, the present invention provides purified polypeptides comprising an ubiquitination-regulating domain. The invention also provides methods of using such polypeptides for screening for agents, for producing antibodies, and for treatment of diseases, e.g., proliferative diseases, neurodegenerative diseases, autoimmune diseases, metabolic disease and developmental abnormalities. The invention further provides antibodies that bind an ubiquitination-regulating domain and agents and antibodies that regulate ubiquitination in cells, e.g., by modulating the interaction between a TSG101 protein and an MDM2 protein.

13 Claims, 8 Drawing Sheets

OTHER PUBLICATIONS

Koonin, et al. "*TSG101 may be the prototype of a class of dominant negative ubiquitin regulators*", Nature Genetics vol. 16: 330-331 (1997).

Kubbuat, et al. "*Regulation of p53 stability by Mdm2*", Nature vol. 387: 299-303 (1997).

Lane, et al. "*MDM2—arbiter of p53's destruction*", Trends Biochem. Sci. vol. 22: 372-374 (1997).

Lee, et al. "*Aberrant splicing but not mutations of TSG101 in human breast cancer*", Cancer Research, vol. 57: 3131-3134 (1997).

Levine, et al. "*The spectrum of mutations at the p53 locus: Evidence for tissue-specific mutagenesis, selection of mutant alleles, and a "gain of function" phenotype*", Ann. NY Acad. Sci. vol. 768: 111-128 (1995).

Levine. "*p53, the cellular gatekeeper for growth and division*", Cell vol. 88: 323-331 (1997).

Li, et al. "*tsg 101: A novel tumor susceptibility gene isolated by controlled homozygous functional knockout of allelic loci in mammalian cells*", Cell vol. 85: 319-329 (1996).

McMasters, et al. "*mdm2 deletion does not alter growth characteristics of p53-deficient embryo fibroblasts*", Oncogene vol. 13: 1731-1736 (1996).

Montes De Oca Luna, et al. "*Rescue of early embryonic lethality in mdm2-deficient mice by deletion of p53*", Nature vol. 378: 203-206 (1995).

Olson, et al. "*identification and characterization of multiple mdm-2 proteins and mdm-2-p53 protein complexes*" Oncogene vol. 8: 2353-2360 (1993).

Oren, "*Regulation of the p53 tumor suppressor protein*", J. Biol. Chem. vol. 274(51): 36031-36034 (1999).

Ponting, et al. "*The breast cancer gene product TSG101: A regulator of ubiquitination?*", J. Mol. Med. vol. 75: 467-469 (1997).

Prives. "*The MDM2-p53 circuit*", Cell vol. 95: 5-8 (1998).

Roth, et al. "*Nucleo-cytoplasmic shuttling of the hdm2 oncoprotein regulates the levels of the p53 protein via a pathway used by the human immunodeficiency virus rev protein*", The EMBO J. vol. 17(2): 554-564 (1998).

Ruland, et al. "*p53 accumulation, defective cell proliferation, and early embryonic lethality in mice lacking tsq101*", PNAS vol. 98(4): 1859-1864 (2001).

Sherr, et al. "*The ARF/p53 pathway*", Curr. Opin. Genet. Dev. vol. 10: 94-99 (2000).

Sun, et al. "*Frequent abnormalities of TSG101 transcripts in human prostate cancer*", Oncogene vol. 15: 3121-3125 (1997).

Sun, et al. "*Tumor susceptibility gene 101 protein represses androgen receptor transactivation and interacts with p300*", Cancer vol. 86: 689-696 (1999).

Turpin, et al. "Stress-induced aberrant splicing of TSG101: Association to high tumor grade and p53 status in breast cancers", Oncogene vol. 18: 7834-7837 (1999).

Vandemark, et al. "*Molecular insights into polyubiquitin chain assembly: crystal structure of the Mms2/Ubc13 heterodimer*", Cell vol. 105: 711-720 (2001).

Vousden, et al. "*p53: Death Star*", Cell vol. 103: 691-694 (2002).

Wagner, et al. "*Genomic architecture and transcriptional activation of the mouse and human tumor susceptibility gene TSG101: Common types of shorter transcripts are true alternative splice variants*", Oncogene vol. 17: 2761-2770 (1998).

Ward, et al. "Degradation of CFTR by the ubiquitin-proteasome pathway", Cell vol. 83: 121-127 (1995).

Watanabe, et al. "*A putative tumor suppressor, TSG101, acts as a transcriptional suppressor through its coiled -coil domain*", Biochem. Biophys. Res. Commun. vol. 245: 900-905 (1998).

Weissman. "*Themes and variations on ubiquitylation*", Nature Reviews vol. 2:169-178 (2001).

Xie, et al. "*Cell cycle-dependent subcellular localization of the TSG101 protein and mitotic and nuclear abnormalities associated with TSG101 deficiency*", Proc. Natl. Acad. Sci. USA vol. 95: 1595-1600 (1998).

Zhang, et al. "*ARF promotes MDM2 degradation and stabilizes p53: ARF-INK4a locus deletion impairs both the Rb and p53 tumor suppression pathways*", Cell vol. 92: 725-734 (1998).

\* cited by examiner

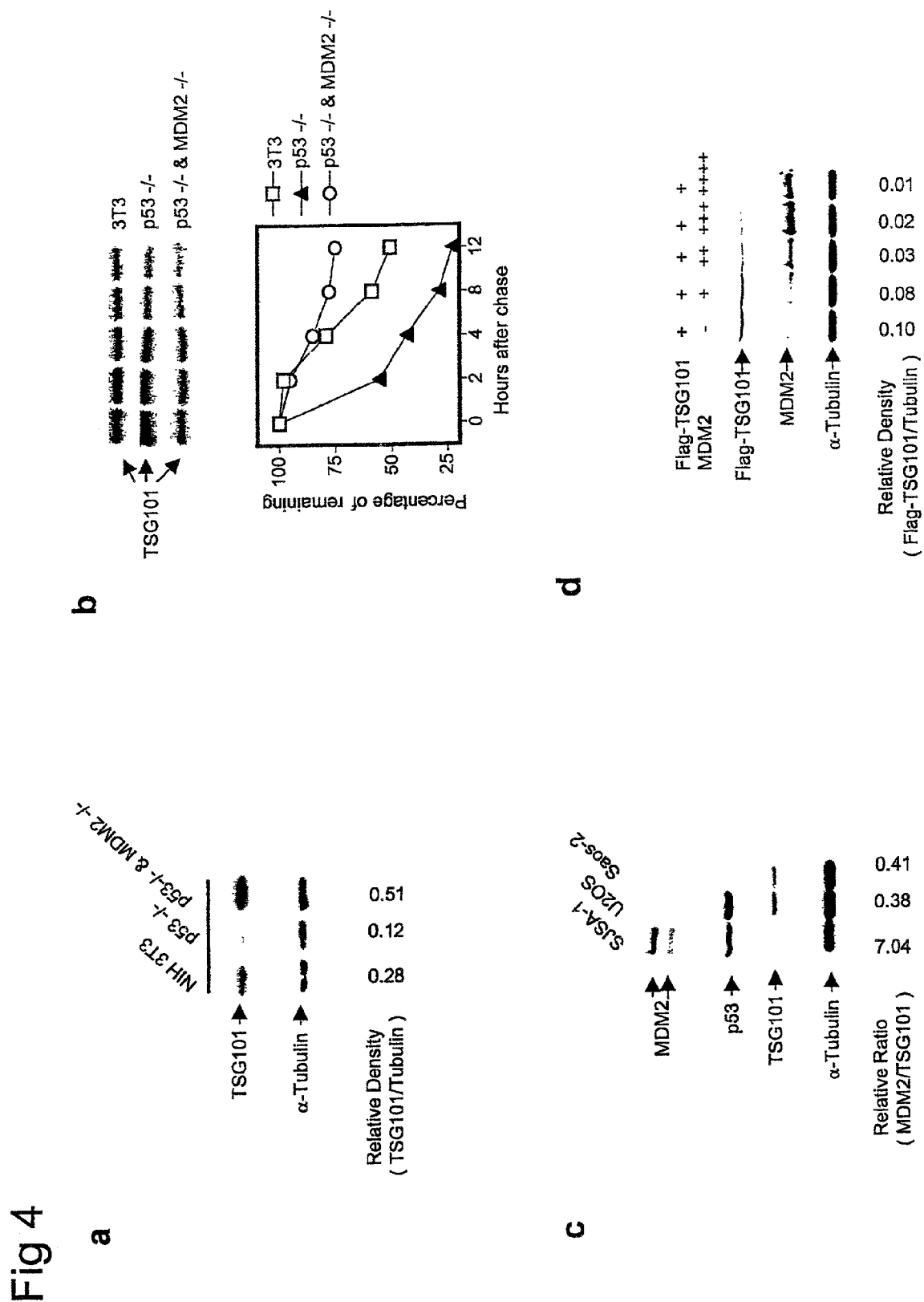

FIGURE 6

SEQ ID NO:1
GenBank Accession No. U82130.1/GI:1772663

MAVSESQLKKMVSKYKYRDLTVRETVNVITLYKDLKPVLDSYVFNDGSSRELM
NLTGTIPVPYRGNTYNIPICLWLLDTYPYNPPICFVKPTSSMTIKTGKHVDANGKI
YLPYLHEWKHPQSDLLGLIQVMIVVFGDEPPVFSRPISASYPPYQATGPPNTSYMP
GMPGGISPYPSGYPPNPSGYPGCPYPPGGPYPATTSSQYPSQPPVTTVGPSRDGTIS
EDTIRASLISAVSDKLRWRMKEEMDRAQAELNALKRTEEDLKKGHQKLEEMVT
RLDQEVAEVDKNIELLKKKDEELSSALEKMENQSENNDIDEVIIPTAPLYKQILNL
YAEENAIEDTIFYLGEALRRGVIDLDVFLKHVRLLSRKQFQLRALMQKARKTAG
LSDLY

SEQUENCE LISTING

<160> NUMBER OF SEQ ID NOS: 5

<210> SEQ ID NO 1
<211> LENGTH: 390
<212> TYPE: PRT
<213> ORGANISM: Homo sapiens

<400> SEQUENCE: 1

```
Met Ala Val Ser Glu Ser Gln Leu Lys Lys Met Val Ser Lys Tyr Lys
  1               5                  10                  15

Tyr Arg Asp Leu Thr Val Arg Glu Thr Val Asn Val Ile Thr Leu Tyr
             20                  25                  30

Lys Asp Leu Lys Pro Val Leu Asp Ser Tyr Val Phe Asn Asp Gly Ser
         35                  40                  45

Ser Arg Glu Leu Met Asn Leu Thr Gly Thr Ile Pro Val Pro Tyr Arg
     50                  55                  60

Gly Asn Thr Tyr Asn Ile Pro Ile Cys Leu Trp Leu Leu Asp Thr Tyr
 65                  70                  75                  80

Pro Tyr Asn Pro Pro Ile Cys Phe Val Lys Pro Thr Ser Ser Met Thr
                 85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
        115                 120                 125

Gln Val Met Ile Val Val Phe Gly Asp Glu Pro Pro Val Phe Ser Arg
    130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
    210                 215                 220

Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
```

-continued

```
                355                 360                 365
Lys Gln Phe Gln Leu Arg Ala Leu Met Gln Lys Ala Arg Lys Thr Ala
    370                 375                 380

Gly Leu Ser Asp Leu Tyr
385                 390

<210> SEQ ID NO 2
<211> LENGTH: 10
<212> TYPE: PRT
<213> ORGANISM: Artificial Sequence
<220> FEATURE:
<223> OTHER INFORMATION: hemagglutinin

<400> SEQUENCE: 2

Cys Tyr Pro Tyr Asp Val Pro Asp Tyr Ala
1               5                   10

<210> SEQ ID NO 3

<400> SEQUENCE: 3

000

<210> SEQ ID NO 4
<211> LENGTH: 11
<212> TYPE: PRT
<213> ORGANISM: Artificial Sequence
<220> FEATURE:
<223> OTHER INFORMATION: c-myc

<400> SEQUENCE: 4

Cys Glu Gln Lys Leu Ile Ser Glu Glu Asp Leu
1               5                   10

<210> SEQ ID NO 5
<211> LENGTH: 8
<212> TYPE: PRT
<213> ORGANISM: Homo sapiens

<400> SEQUENCE: 5

Tyr Pro Tyr Asp Val Pro Asp Tyr
1               5
```

US 7,714,108 B2

MAMMALIAN TUMOR SUSCEPTIBILITY GENE PRODUCTS AND THEIR USES

This application claims the benefit of U.S. Provisional Application No. 60/262,763, filed Jan. 19, 2001.

FIELD OF THE INVENTION

The invention relates to protein ubiquitination, and to mammalian cell proliferation.

BACKGROUND OF THE INVENTION

The TSG101 tumor susceptibility gene initially was identified by the reversible neoplasia associated with deficiency of its protein product in mouse fibroblasts (1). Deficiency of TSG101 induced by antisense RNA in NIH3T3 cells leads to colony formation in 0.5% agar, focus formation in monolayer cell cultures, and the ability to form metastatic tumors in athymic nude mice (1). Turn off of TSG101-inactivating antisense RNA reverses these features of neoplastic transformation as well as the nuclear, microtubule, and mitotic spindle abnormalities observed in TSG101-deficient cells (1, 2). The steady-state level of TSG101 protein normally is regulated post-translationally in cells within a narrow range (3), and overexpression of TSG101 from an adventitious promoter can also lead to cell cycling abnormalities (2) and neoplastic transformation (1). Truncated TSG101 transcripts, which are observed in a variety of human tumors as well as in normal cells (4-7), have been attributed to aberrant or alternative RNA splicing (8) and have been correlated with both cellular stress (4, 5) and mutation of p53 (5). The TSG101 protein contains motifs common to transcription regulators (1) and can modulate transcriptional activation by steroid hormone receptors (9-11).

Sequence analysis has also suggested that TSG101, which is expressed in mammalian cells from the earliest stages of embryonic development and in multiple tissues of adult mice (8), may additionally have a role in the regulation of ubiquitin-mediated proteolysis (12, 13). The N-terminal region of the TSG101 protein contains a domain (Ubc) that resembles the catalytically active region of ubiquitin conjugases (E2 enzymes) but lacks an active site cysteine residue crucial to the function of these enzymes (12-14), leading to speculation that TSG101 may act as a dominant negative inhibitor of ubiquitination (12, 13).

p53 is a key tumor suppressor that transcriptionally activates MDM2 as well as other genes implicated in both cell growth and cell death (15-18). MDM2 in turn negatively regulates p53 by promoting its ubiquitin-mediated degradation (19-21). Despite p53/MDM2 feedback control, p53 accumulates in cells soon after DNA damage, hypoxia, and other types of stress, suggesting that the actions of MDM2 and p53 on each other are themselves regulated (16). Several mechanisms for such regulation have been proposed (16, 17) and recent evidence indicates that alteration of MDM2 stability mediated by its interactions with other cellular proteins may have a role in this process (22-24).

There is a continuing need in the art for new and better methods of modulating proliferation of mammalian cells. The present invention addresses this need.

SUMMARY OF THE INVENTION

The present invention provides methods and compositions for regulating ubiquitination in a cell. In particular, the present invention provides purified polypeptides comprising an ubiquitination-regulating domain. The invention also provides methods of using such polypeptides for screening for agents, for producing antibodies, and for treatment of diseases, e.g., proliferative diseases, neurodegenerative diseases, autoimmune diseases, and developmental abnormalities. The invention further provides antibodies that bind an ubiquitination-regulating domain and agents and antibodies that regulate ubiquitination in cells, e.g., by modulating the interaction between a TSG101 protein and an MDM2 protein.

In one embodiment, the present invention provides antibodies that bind specifically to a polypeptide comprising an ubiquitination-regulating domain. In a preferred embodiment, the invention provides antibodies that bind to the ubiquitination-regulating domain, or a functional fragment thereof, of a TSG101 protein, e.g., a human TSG101 protein. In another preferred embodiment, the invention provides antibodies that bind to an ubiquitination-regulating domain comprising amino acid residues 1-140 of a human TSG101 protein, e.g., amino acid residues 1-140 of SEQ ID NO:1. In still another preferred embodiment, the ubiquitination-regulating domain comprises amino acid residues 50-140 of a human TSG101, e.g., amino acid residues 50-140 of SEQ ID NO:1. In still another preferred embodiment, the invention provides antibodies that bind to an ubiquitination-regulating domain comprising amino acid residues 140-250 of a human TSG101 protein, e.g., amino acid residues 140-250 of SEQ ID NO:1. In still other embodiments, the ubiquitination-regulating domain may comprises, e.g., amino acid residues 10-140, 20-140, 30-140, 40-140, 1-160, 1-180, 1-200, 1-220, 50-250 or 1-250 of a human TSG101, e.g., amino acid residues 10-140, 20-140, 30-140, 40-140, 1-160, 1-180, 1-200, 1-220, 50-250 or 1-250 of SEQ ID NO:1. The present invention also provides methods of producing such antibodies that binds specifically to an ubiquitination-regulating domain. In the methods of the invention, antibodies are raised against a polypeptide comprising the ubiquitination-regulating domain. Any polypeptide that comprises an ubiquitination-regulating domain can be used to produce the antibodies of the invention.

In other embodiments, the present invention provides antibodies that bind a TSG101 protein at a domain other than the Ubc domain, e.g., at the coiled-coil domain, or the steady box domain such that the binding modulates the function of the ubiquitination-regulating domain.

The present invention also provides a cell comprising a polynucleotide encoding an ubiquitination-regulating domain operationally linked to a regulatory sequence such that the cell expresses the ubiquitination-regulating domain. The invention also provides a cell comprising (i) a polynucleotide encoding an ubiquitination-regulating domain operationally linked to a regulatory sequence; and (ii) a polynucleotide encoding MDM2 protein operationally linked to a regulatory sequence, such that the cell expresses the ubiquitination-regulating domain and the MDM2 protein. The invention also provides a cell comprising (i) a polynucleotide encoding an ubiquitination-regulating domain operationally linked to a regulatory sequence; (ii) a polynucleotide encoding MDM2 protein operationally linked to a regulatory sequence; and (iii) a polynucleotide encoding p53 protein operationally linked to a regulatory sequence, such that the cell expresses the ubiquitination-regulating domain, the MDM2 protein, and the p53 protein. The ubiquitination-regulating domain can be an ubiquitination-regulating domain, or a functional fragment thereof, of a TSG101 protein, e.g., a human TSG101 protein. In a preferred embodiment, the ubiquitination-regulating domain comprises amino acid residues 1-140 of a human TSG101 protein, e.g., amino acid residues 1-140 of SEQ ID NO:1. In another preferred embodiment, the ubiquitination-regulating domain comprises amino acid residues 50-140 of a human TSG101, e.g., amino acid residues 50-140 of SEQ ID NO:1. In still another preferred embodiment, the ubiquitination-regulating domain comprises amino acid residues 140-250 of a human TSG101 protein, e.g., amino acid residues 140-250 of SEQ ID NO:1. In still other embodiments, the ubiquitination-regulating domain may comprises amino acid residues 10-140, 20-140, 30-140, 40-140, 1-160, 1-180, 1-200, 1-220, 50-250 or 1-250 of a human TSG101, e.g., amino acid residues 10-140, 20-140, 30-140, 40-140, 1-160, 1-180, 1-200, 1-220, 50-250 or 1-250 of SEQ ID NO:1.

The invention provides methods of identifying an agent that modulates the interaction of a TSG101 protein with an MDM2 protein. The methods comprise screening candidate agents using a screening assay comprising a cell expressing MDM2 and a polypeptide comprising an ubiquitination-regulating domain, or a functional fragment thereof, of the TSG101 protein. In a specific embodiment, the invention provides a method of identifying an agent that is capable of modulating the interaction of a TSG101 protein with MDM2, comprising: (a) contacting a cell expressing MDM2 and a polypeptide comprising an ubiquitination-regulating domain, or a functional fragment thereof, of the TSG101 protein with the agent and measuring MDM2 level in the cell; (b) contacting a cell expressing MDM2 but not an ubiquitination-regulating domain, or a functional fragment thereof, of the TSG101 protein, with the agent and measuring MDM2 level in the cell; and (c) comparing MDM2 levels measured in (a) and (b). A difference in MDM2 levels as determined in step (c) identifies the agent as capable of modulating the interaction of the TSG101 protein with MDM2.

The invention also provides methods of modulating a level of MDM2 or p53 in a cell. The methods comprise contacting the cell with a polypeptide or derivative thereof that comprises a polypeptide comprising an ubiquitination-regulating domain.

The invention also provides methods of modulating a level of MDM2, or TSG101, or p53 in a cell. The methods comprise contacting the cell with an agent that is capable of modulating the interaction of a TSG101 protein with MDM2.

The invention further provides methods for treating a subject of a disease or any other undesirable conditions that are a result of a deviation of a level of TSG101, or MDM2, or p53 from normal ranges. The subject that can be treated includes a human or a non-human mammal.

In one embodiment, the invention provides methods for treating a subject of a condition resulting from a change in a level of MDM2 protein in cells of the subject. The methods comprise administering to the subject a therapeutically effective amount of an agent which comprises an ubiquitination-regulating domain.

In another embodiment, the invention provides methods of treating a subject of a condition resulting from a change in a level of a TSG101 protein in cells of the subject. The methods comprising administering to the subject a therapeutically effective amount of an agent, said agent modulating the interaction of said TSG101 protein with MDM2.

In still another embodiment, the invention provides methods for treatment of a proliferative disease in a subject comprising: (a) monitoring the subject for a level of p53; and (b) treating the subject with an agent which comprises an ubiquitination-regulating domain so as to maintain the level of p53 within a target range.

The invention also provides methods for treating a subject of a proliferative disease. The methods comprise administering to the subject a therapeutically effective amount of an agent that is capable of modulating the interaction between TSG101 and MDM2. In a specific embodiment, the invention provides a method for treatment of a proliferative disease in a subject comprising: (a) monitoring the subject for a level of TSG101; and (b) treating the subject with an agent which is capable of modulating the interaction of the TSG101 with MDM2 so as to maintain the level of TSG101 within a target range.

In any of the methods of the invention where an ubiquitination-regulating domain is used, the ubiquitination-regulating domain can be an ubiquitination-regulating domain, or a functional fragment thereof, of a TSG101 protein, e.g., a human TSG101 protein. In a preferred embodiment, the ubiquitination-regulating domain comprises amino acid residues 1-140 of a human TSG101 protein, e.g., amino acid residues 1-140 of SEQ ID NO:1. In another preferred embodiment, the ubiquitination-regulating domain comprises amino acid residues 50-140 of a human TSG101, e.g., amino acid residues 50-140 of SEQ ID NO:1. In another preferred embodiment, the ubiquitination-regulating domain comprises amino acid residues 140-250 of a human TSG101 protein, e.g., amino acid residues 140-250 of SEQ ID NO:1. In still other embodiments, the ubiquitination-regulating domain may comprises amino acid residues 10-140, 20-140, 30-140, 40-140, 1-160, 1-180, 1-200, 1-220, 50-250 or 1-250 of a human TSG101, e.g., amino acid residues 10-140, 20-140, 30-140, 40-140, 1-160, 1-180, 1-200, 1-220, 50-250 or 1-250 of SEQ ID NO:1.

BRIEF DESCRIPTION OF THE DRAWINGS

FIG. 6 depicts the 390 amino acid sequence of human TSG101 protein (SEQ ID NO:1). (GenBank® Accession No. U82130.1/GI:1772663)

DETAILED DESCRIPTION OF THE INVENTION

Figure 1:
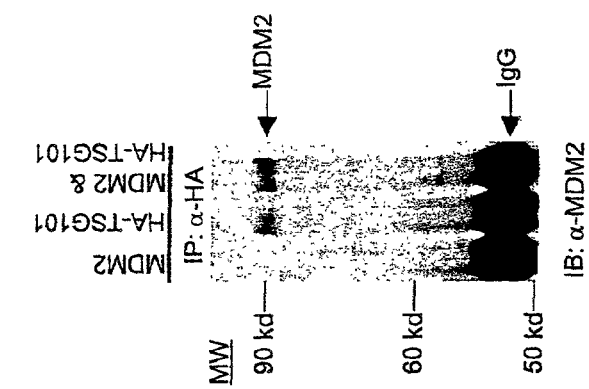
FIGS. 1A-1D depict the results of Western blot analysis of the interaction of TSG101 with p53 and MDM2.
Figure 1:
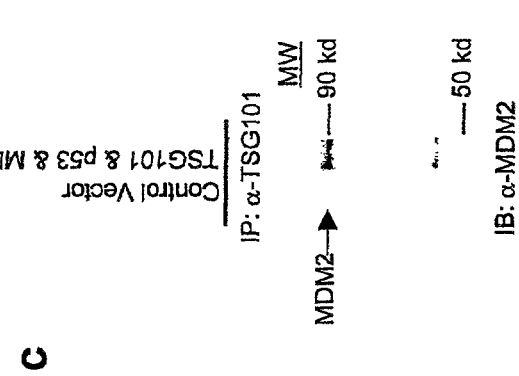
Figure 1:

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a cell" includes a plurality of such cells and reference to "the polynucleotide" includes reference to one or more polynucleotides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein the term "isolated," when used in the context of an antibody, a recombinant host cell, an isolated polypeptide, etc, is meant to describe an antibody, host cell, polypeptide, etc., that is in an environment different from that in which the antibody, host cell, or polypeptide naturally occurs. "Isolated" is meant to include antibodies, host cells, polypeptides, etc., that are within samples that are substantially enriched for the antibody, host cell, or polypeptide of interest and/or in which the antibody, host cell, polypeptide of interest is partially or substantially purified.

As used herein, the term "substantially purified" refers to a substance, e.g., an antibody or other polypeptide, that is removed from its natural environment and is at least 60% free, preferably 75% free, and most preferably 90% free from other components with which it is naturally associated.

The term "binds specifically," in the context of antibody binding, refers to high avidity and/or high affinity binding of an antibody to a specific polypeptide i.e., a ubiquitination-regulating polypeptide. Antibody binding to an epitope on a specific ubiquitination-regulating polypeptide is preferably stronger than binding of the same antibody to any other epitope, particularly those which may be present in molecules in association with, or in the same sample, as the specific polypeptide of interest, e.g., binds more strongly to a specific ubiquitination-regulating polypeptide epitope than to a different epitope so that by adjusting binding conditions the antibody binds almost exclusively to the specific ubiquitination-regulating polypeptide epitope and not to any other epitopes, and not to any other polypeptide which does not comprise the epitope. Antibodies which bind specifically to a subject polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, antibodies of the invention which bind to a specific ubiquitination-regulating polypeptide with a binding affinity of $10^{-7}$ M or more, preferably $10^{-8}$ M or more (e.g., $10^{-9}$ M, $10^{-10}$, $10^{-11}$, etc.). In general, an antibody with a binding affinity of $10^{-6}$ M or less is not useful in that it will not bind an antigen at a detectable level using conventional methodology currently used.

The term "treatment" is used herein to encompass any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

By "subject" or "individual" or "patient" is meant any mammalian subject for whom diagnosis or therapy is desired, particularly humans. Other subjects may include cattle, dogs, cats, guinea pigs, rabbits, rats, mice, horses, and so on.

For simplicity reasons, this disclosure often makes references to a gene or protein by its generic name. In such cases, it will be understood that the disclosure is equally applicable to any mammalian homologs of the gene or protein. This disclosure also often makes references to a gene or protein by its name for a specific species. In such cases, unless specifically indicated, it will be understood that the disclosure is equally applicable to any other mammalian homologs of the gene or protein. For example, unless specifically indicated, MDM2 will be understood to encompass any mammalian homolog of the MDM2 protein.

Overview

The p53 tumor suppressor protein and the MDM2 oncoprotein form a feedback-control loop that up-regulates cellular MDM2 production, blocks p53 activity, and promotes p53 decay. Tsg101 was discovered as a gene whose deficiency results in neoplastic transformation of NIH3T3 cells and the ability to generate metastatic tumors in nude mice. Its protein product contains a domain, Ubc, characteristic of the catalytic domain of ubiquitin conjugase (E2) enzymes but lacking an active site cysteine crucial for ubiquitin conjugase activity. Defective regulation of ubiquitination has been implicated in diseases including neurodegenerative diseases, autoimmune diseases, developmental abnormalities, metabolic disease and cancers (see, e.g., reference 41). The amino residues 140-250 of TSG101 includes a proline-rich domain which has been suggested to be a binding site for other proteins, such as NEDD4 (a developmentally regulated ubiquitin-protein ligase). NEDD4 targets the epithelial sodium channel (ENaC), a key regulator of blood sodium concentration, for ubiquitin-mediated turnover (see, Staub et. al., EMBO J. 1996, 15:2371-80). Here we report that an ubiquitination-regulating domain, e.g., the Ubc domain of a TSG101, regulates ubiquitination in a cell. Such regulation may play a role in, e.g., regulation of ubiquitin-mediated proteolysis, translation, DNA repair, activation of transcription of factors and kinases, and translocation (see, e.g., references 40, 41). For example, we show that TSG101 participates with MDM2 in a separate autoregulatory loop that modulates the cellular levels of both proteins, and also of p53, by affecting protein decay. We show that the Ubc domain, or a functional fragment thereof (e.g., a biologically-active fragment), of TSG101 interferes with ubiquitination of MDM2, that TSG101 inhibits MDM2 decay and elevates its steady-state level, and that these events are associated with down regulation of p53 protein. Conversely, pulse chase and Western blot experiments in wild type and mutant fibroblasts indicate that elevation of MDM2 by overexpression of wild type p53, by amplification of the endogenous MDM2 gene, or by transfection of MDM2-expressing constructs promotes TSG101 loss, which we show occurs by 26S proteasome-dependent decay. Our results identify TSG101 as both a regulator of, and target of, MDM2/p53 circuitry.

Specific aspects of the invention will now be described in more detail.

Polypeptide Compositions

In some embodiments, the invention provides isolated polypeptides comprising a ubiquitination-regulating domain. The subject polypeptides are useful as immunogens, to generate antibodies to a ubiquitination-regulating polypeptide, as described in more detail below. The subject polypeptides (referred to as "ubiquitination-regulating polypeptides") are also useful to reduce ubiquitination of MDM2 polypeptide in a cell, thereby increasing the level of MDM2 polypeptide in the cell. For example, a subject expression vector comprising a subject polynucleotide (described in more detail below) encoding a subject ubiquitination-regulating polypeptide (which may be a fusion protein) is introduced into a host cell, where the subject polypeptide is produced. The subject polypeptide regulates ubiquitination of one or more proteins in the cell.

As used herein, an ubiquitination-regulating domain refers to a polypeptide which regulates ubiquitination, e.g., via regulating ubiquitin conjugases (E2 enzymes). In some of these embodiments, the ubiquitination-regulating domain has the amino acid sequence of an ubiquitination-regulating domain of a TSG101, e.g., an ubiquitination-conjugase-like Ubc domain of a human TSG101. In some embodiments, the ubiquitination-regulating domain has the amino acid sequence of a functional fragment of an ubiquitination-regulating domain of a TSG101, e.g., a human TSG101 (SEQ ID NO:1; GenBank Accession No. U82130.1/GI:1772663).

As used herein, a functional fragment of an ubiquitination-conjugase-like Ubc domain refers to any fragment of the Ubc domain that regulates ubiquitination. Fragments having such activity are readily determined by, e.g., methods as described in the application. In one embodiment, the ubiquitination-regulating domain comprises amino acid residues 1-140 of a human TSG101 protein, e.g., amino acid residues 1-140 of SEQ ID NO:1. In another embodiment, the ubiquitination-regulating domain comprises amino acid residues 50-140 of a human TSG101, e.g., amino acid residues 50-140 of SEQ ID NO:1. In still another embodiment, the ubiquitination-regulating domain comprises amino acid residues 140-250 of a human TSG101, e.g., amino acid residues 140-250 of SEQ ID NO:1. In still other embodiments, the ubiquitination-regulating domain may comprises, e.g., amino acid residues 10-140, 20-140, 30-140, 40-140, 1-160, 1-180, 1-200, 1-220, 50-250 or 1-250 of a human TSG101, e.g., amino acid residues 10-140, 20-140, 30-140, 40-140, 1-160, 1-180, 1-200, 1-220, 50-250 or 1-250 of SEQ ID NO:1. The nucleotide and amino acid sequences of TSG101 are also disclosed in U.S. Pat. No. 5,891,668. The construct designated TSG101B in the Examples comprises an insert that is largely a TSG101 Ubc domain, and is an example of an ubiquitination-regulating domain. Alternatively, an ubiquitination-regulating domain may be an Ubc domain from an ubiquitin conjugase that is altered to lack the active site cysteine that is critical for the function of a ubiquitin conjugase.

A subject ubiquitination-regulating polypeptide can be provided as a fusion protein, e.g., where the subject ubiquitination-regulating polypeptide is fused in-frame to a heterologous polypeptide (e.g., a polypeptide other than a TSG101 polypeptide). The subject ubiquitination-regulating polypeptide is fused in-frame at the carboxyl terminal or the amino terminal of the heterologous protein ("the fusion partner"), or is fused in-frame at an internal site in the fusion partner. Fusion partners can be those that provide for a specific function, e.g., localization of the fusion protein to a particular subcellular compartment; stabilization of the fusion protein; binding of the fusion protein to another protein, to a nucleic acid, to a carbohydrate moiety on a protein, etc.; enzymatic activity; and the like.

A fusion partner polypeptide can be a natural or non-natural (e.g., having an amino acid sequence not found in nature) polypeptide; a polypeptide from an animal, plant, eubacterium, archaebacterium, fungus, protozoa, or virus. A fusion partner polypeptide can be a fragment of any known naturally-occurring or non-naturally occurring polypeptide. Fragments or interest include, but are not limited to, functional domains, e.g., a catalytic domain of an enzyme, a DNA-binding domain of a transcription factor, a ligand-binding domain of a receptor, and the like; structural domains; fragments that inhibit a protein function; and the like.

A subject fusion protein may comprise, in addition to a fusion partner polypeptide and a ubiquitination-regulating polypeptide, an immunological tag. An immunological tag, if present, is present at the amino terminus, the carboxyl terminus, or disposed between the fusion partner polypeptide and the metal ion affinity peptide. Immunological tags are known in the art, and are typically a sequence of between about 6 and about 50 amino acids that comprise an epitope that is recognized by an antibody specific for the epitope. Non-limiting examples of such tags are hemagglutinin (HA; e.g., CYPYDVPDYA, SEQ ID NO: 2), FLAG (e.g., DYKDDDDK, SEQ ID NO: 3), c-myc (e.g., CEQKLISEEDL, SEQ ID NO: 4), and the like.

Production of Subject Polypeptides

The subject polypeptides can be produced synthetically, or can be produced recombinantly, i.e., a polynucleotide comprising a coding region encoding a polypeptide comprising an ubiquitination-regulating domain can be inserted into an expression vector, and the ubiquitination-regulating domain-coding region transcribed and translated.

Ubiquitination-regulating domain-containing polypeptides can be produced synthetically, using any known method. One may employ solid phase peptide synthesis techniques, where such techniques are known to those of skill in the art. See Jones, The Chemical Synthesis of Peptides (Clarendon Press, Oxford)(1994). Generally, in such methods a peptide is produced through the sequential addition of activated monomeric units to a solid phase bound growing peptide chain.

For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the polynucleotide comprising a nucleotide sequence encoding a polypeptide comprising a ubiquitination-regulating domain, and a transcriptional termination region. After introduction of the DNA, the cells containing the construct may be selected by means of a selectable marker, the cells expanded and then used for expression.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the protein will benefit from native folding and post-translational modifications. Small peptides can also be synthesized in the laboratory. Polypeptides that are subsets of the complete amino acid sequence may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique.

Polynucleotides and Host Cells

The invention further provides polynucleotides, particularly isolated polynucleotides, comprising a nucleotide sequence encoding a polypeptide comprising a ubiquitination-regulating domain, as well as recombinant vectors ("constructs") comprising such polynucleotides. Recombinant vectors are useful for propagation of the subject polynucleotides (cloning vectors). They are also useful for effecting expression of a subject polynucleotide in a cell (expression vectors), such that a subject polypeptide is produced in the cell. Some vectors accomplish both cloning and expression functions. The choice of appropriate vector is well within the skill of the art. Many such vectors are available commercially. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons.

The subject polynucleotides encode a subject ubiquitination-regulating polypeptide, e.g., a polypeptide that comprises a ubiquitination-regulating domain, e.g., amino acid residues 1-140, 50-140, 140-250, 10-140, 20-140, 30-140, 40-140, 1-160, 1-180, 1-200, 1-220, 50-250 or 1-250 of a TSG101 protein, e.g., amino acid residues 1-140, 50-140, 140-250, 10-140, 20-140, 30-140, 40-140, 1-160, 1-180, 1-200, 1-220, 50-250 or 1-250 of a protein having the amino acid sequence set forth in SEQ ID NO:01. In some embodiments, a subject polynucleotide encodes a subject fusion protein.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc.

Constructs are introduces into a host cell using standard methods, including calcium phosphate precipitation, electroporation, lipofection, infection (where the vector is a viral vector) and the like.

The invention further provides a host cell comprising a subject recombinant vector. The present invention further provides host cells, which may be isolated host cells, comprising a polynucleotide of the invention. Suitable host cells include prokaryotes such as *E. coli, B. subtilis*, eukaryotes, including insect cells in combination with baculovirus vectors, yeast cells, such as *Saccharomyces cerevisiae*, or cells of a higher organism such as vertebrates, including amphibians (e.g., *Xenopus laevis* oocytes), and mammals, particularly mammals, e.g. COS cells, CHO cells, 293 cells, 3T3 cells, and the like, may be used as the expression host cells. Host cells can be used for the purposes of propagating a subject polynucleotide, for production of a subject polypeptide, or in cell-based methods for identifying agents which modulate a level of subject mRNA and/or protein and/or activity in a cell.

Antibodies to a Ubiquitination-Regulating Domain

A ubiquitination-regulating domain of the invention may be used as an immunogen to generate antibodies which immunospecifically bind such an immunogen. Such antibodies include but are not limited to polyclonal, monoclonal, chimeric, single chain, Fab fragments, and an Fab expression library. Such antibodies are useful in modulating the interaction between the ubiquitination-regulating domain and other proteins in a cell, e.g., an MDM2 protein and/or a p53 protein. In many embodiments, an antibody of the invention is isolated.

In a specific embodiment, antibodies to an ubiquitination-regulating domain comprising the ubiquitination-regulating domain, or a functional fragment thereof, of a human TSG101 protein are produced. In another embodiment, antibodies to a polypeptide comprising amino residues 1-140 of a human TSG101 protein, e.g., amino acid residues 1-140 of SEQ ID NO:1, are produced. In yet another embodiment, antibodies to a polypeptide comprising amino residues 140-250 of a human TSG101 protein, e.g., amino acid residues 140-250 of SEQ ID NO:1, are produced. In still another embodiment, antibodies to a polypeptide comprising amino residues 50-140 of a human TSG101 protein, e.g., amino acid residues 50-140 of SEQ ID NO:1, are produced.

Various procedures known in the art may be used for the production of polyclonal antibodies to an ubiquitination-regulating domain. In a particular embodiment, rabbit polyclonal antibodies to an ubiquitination-regulating domain, e.g., the ubiquitination-regulating domain, or a subsequence thereof, of a human TSG101 protein can be obtained. For the production of antibody, various host animals can be immunized by injection with a native ubiquitination-regulating domain, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed to an ubiquitination-regulating domain, or a fragment thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (see e.g., PCT/US90/02545). According to the invention, human antibodies may be used and can be obtained by using human hybridomas (Cole et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314: 452-454) by splicing the genes from a mouse antibody molecule specific for a human ubiquitination-regulating domain together with genes from a human antibody molecule of appropriate biological activity can be used; such antibodies are within the scope of this invention.

According to the invention, techniques described for the production of single chain antibodies (U.S. Pat. No. 4,946,778) can be adapted to produce ubiquitination-regulating domain-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for an ubiquitination-regulating domain.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art (e.g., enzyme-linked immunosorbent assay or ELISA). For example, to select antibodies which recognize a specific domain of an ubiquitination-regulating domain, one may assay generated hybridomas for a product which binds to an ubiquitination-regulating domain containing such domain.

Antibodies specific to an epitope of an ubiquitination-regulating domain are also provided.

The foregoing antibodies can be used in methods known in the art relating to the activity of an ubiquitination-regulating domain of the invention, e.g., for determination interaction partners of these proteins, measuring levels thereof in appropriate physiological samples, in diagnostic methods, etc.

Compositions

The present invention further provides compositions, including pharmaceutical compositions, comprising the polypeptides, polynucleotides, agents, recombinant vectors, and host cells of the invention. These compositions may include a buffer, which is selected according to the desired use of the polypeptide, agent, polynucleotide, recombinant vector, or host cell, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Screening Assays

The present invention provides screening methods for identifying agents, e.g., antibodies and small molecules, which modulate a TSG101 interaction with MDM2 in a cell, and in particular, agents that modulate binding of a TSG101 ubiquitination domain to an MDM2 polypeptide. In general, the assays are in vitro assays. In some embodiments, the assays are cell free assays, and utilize MDM2 polypeptide, and a TSG101 polypeptide or a ubiquitination-regulating polypeptide of the invention.

As used herein, the term "modulate" encompasses "increase" and "decrease". In some embodiments, agents which reduce TSG101/MDM2 interaction in a cell are of interest. Such agents may be of interest as candidates for promoting cell division, reducing apoptosis, or reducing growth arrest.

The terms "agent", "substance" and "compound" are used interchangeably herein. Candidate agents encompass numerous chemical classes, which may be synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The present invention also provides methods for identifying cellular proteins that interact with an ubiquitination-regulating domain. Any methods known in the art, including but are not limited to, yeast two-hybrid assays (see, e.g., Fields and Song, 1989, Nature 340:245-246 and U.S. Pat. No. 5,283,173), immunoprecipitation, Western blot (see, example section below), can be used for this purpose.

Agents that have an effect in a subject assay method are selected for further study, and assessed for cellular availability, cytotoxicity, biocompatibility, etc.

Cell-Free In Vitro Assays

In some embodiments, the screening methods are cell-free in vitro screening methods. These methods generally involve contacting a TSG101 protein or a subject ubiquitination-regulating polypeptide, and an MDM2 polypeptide with a test agent; and determining the effect, if any, on binding of the TSG101 protein or ubiquitination-regulating polypeptide, to the MDM2 polypeptide. A reduction in binding between the two proteins, compared to a control in the absence of the test agent, is an indication that the agent reduces binding.

Whether a ubiquitination-regulating polypeptide binds to an MDM2 polypeptide can be determined using an immunological assay, e.g., where an antibody specific for one of the two proteins is used. A variety of immunological assays can be used, including, but not limited to, enzyme-linked immunosorbent assays, immunoprecipitation, Western blotting, and the like. If desired, one of the proteins, e.g., the ubiquitination-regulating polypeptide, can be provided with an immunological "tag," as described above, and antibodies specific for the tag can be used in an immunological assay. Alternatively, the ubiquitination-regulating polypeptide can be fused in-frame to a histidine tag (e.g., $(His)_6$, and the like), and binding to a metal ion can be used to detect formation of ubiquitination-regulating polypeptide/MDM2 binding. Still further, one of the two proteins, e.g., the ubiquitination-regulating polypeptide, can be labeled with a member of a specific binding pair, e.g., biotin, and the like, and binding of the ubiquitination-regulating polypeptide to the MDM2 protein can be detected using the complementary member of the specific binding pair, as described above.

Cell-Based In Vitro Assay Methods

The invention further provides cell-based in vitro screening methods for identifying an agent that modulates binding of a ubiquitination-regulating domain to an MDM2 protein. The methods generally involve contacting a cell expressing MDM2 and a polypeptide comprising an ubiquitination-regulating domain, or a functional fragment thereof, of the TSG101 protein, with a test agent; and determining the effect, if any, of the test agent on binding of the ubiquitination-regulating domain to the MDM2 protein.

In a specific embodiment, the method comprises: (a) contacting a cell producing MDM2 polypeptide and a polypeptide comprising an ubiquitination-regulating domain, or a functional fragment thereof, of the TSG101 protein with a test agent; and (b) determining the effect, if any of the test agent on the level of MDM2 polypeptide in the cell, compared to a suitable control. A suitable control is a cell that produces the MDM2 polypeptide, and the polypeptide comprising an ubiquitination-regulating domain, or a functional fragment thereof, of the TSG101 protein, in the absence of the test agent. In the absence of the test agent, the level of MDM2 polypeptide is expected to be relatively high. In the presence of a test agent that reduces the binding of MDM2 to the ubiquitination-regulating domain, the level of MDM2 is expected to be lower than in the cell in the absence of the test agent.

Cells that produce MDM2 and a polypeptide comprising an ubiquitination-regulating domain, or a functional fragment thereof, of the TSG101 protein are described herein.

In Vivo Screening Methods

Screening may also be performed on organisms expressing various levels of TSG101. In this regard, TSG101 heterozygous and homozygous knockout mice as described (38) may be used.

Agents

The invention further provides agents identified using a screening assay of the invention, and compositions comprising the agents, including pharmaceutical compositions. The agents are useful for modulating binding of a ubiquitination-regulating domain and MDM2.

The subject compositions can be formulated using well-known reagents and methods. In some embodiments, compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Methods

The invention provides methods for modulating mammalian cell proliferation; methods of modulating interaction of TSG101 with MDM2 in a mammalian cell; methods of modulating the rate of decay of MDM2 in a cell; methods of modulating a level of p53 polypeptide in a cell; methods of modulating ubiquitination of a polypeptide in a cell; and methods of maintaining a level of TSG101 in a cell.

The invention also provides methods of modulating a level of MDM2 or p53 in a cell. The methods comprise contacting the cell with a polypeptide or derivative thereof that comprises a polypeptide comprising an ubiquitination-regulating domain.

The invention also provides methods of modulating a level of MDM2, or TSG101, or p53 in a cell. The methods comprise contacting the cell with an agent that is capable of modulating the interaction of a TSG101 protein with MDM2.

The invention further provides methods for treating a subject of a disease or any other undesirable conditions that are a result of a deviation of a level of TSG101, or MDM2, or p53 from normal ranges. The subject that can be treated includes a human or a non-human mammal.

In one embodiment, the invention provides methods for treating a subject of a condition resulting from a change in a level of MDM2 protein in cells of the subject. The methods comprise administering to the subject a therapeutically effective amount of an agent which comprises an ubiquitination-regulating domain.

In another embodiment, the invention provides methods of treating a subject of a condition resulting from a change in a level of a TSG101 protein in cells of the subject. The methods comprising administering to the subject a therapeutically effective amount of an agent, said agent modulating the interaction of said TSG101 protein with MDM2.

In still another embodiment, the invention provides methods for treatment of a proliferative disease in a subject comprising: (a) monitoring the subject for a level of p53; and (b) treating the subject with an agent which comprises an ubiquitination-regulating domain so as to maintain the level of p53 within a target range.

The invention also provides methods for treating a subject of a proliferative disease. The methods comprise administering to the subject a therapeutically effective amount of an agent that is capable of modulating the interaction between TSG101 and MDM2. In a specific embodiment, the invention provides a method for treatment of a proliferative disease in a subject comprising: (a) monitoring the subject for a level of TSG101; and (b) treating the subject with an agent which is capable of modulating the interaction of the TSG101 with MDM2 so as to maintain the level of TSG101 within a target range.

In any of the methods of the invention where an ubiquitination-regulating domain is used, the ubiquitination-regulating domain can be an ubiquitination-regulating domain, or a functional fragment thereof, of a TSG101 protein, e.g., a human TSG101 protein. In a preferred embodiment, the ubiquitination-regulating domain comprises amino acid residues 1-140 of a human TSG101 protein, e.g., amino acid residues 1-140 of SEQ ID NO:1. In another preferred embodiment, the ubiquitination-regulating domain comprises amino acid residues 50-140 of a human TSG101, e.g., amino acid residues 50-140 of SEQ ID NO:1. In another preferred embodiment, the ubiquitination-regulating domain comprises amino acid residues 140-250 of a human TSG101 protein, e.g., amino acid residues 140-250 of SEQ ID NO:1. In still other embodiments, the ubiquitination-regulating domain may comprises amino acid residues 10-140, 20-140, 30-140, 40-140, 1-160, 1-180, 1-200, 1-220, 50-250 or 1-250 of a human TSG101, e.g., amino acid residues 10-140, 20-140, 30-140, 40-140, 1-160, 1-180, 1-200, 1-220, 50-250 or 1-250 of SEQ ID NO:1.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Materials and Methods

Plasmid and Vector Construction. Full-length human TSG101 cDNA was inserted into the pLLEXP1 vector (1) between the cytomegalovirus promoter and polyadenylation site. HA-tagged (human influenza hemagglutinin peptide, YPYDVPDY, SEQ ID NO: 5), Flag-tagged and c-Myc tagged TSG101 and TSG101 deletion mutant cDNAs were generated by PCR and were also cloned using pLLEXP1. Vectors expressing human wild type p53 (pC53-5N3) (25), human mutant p53 (pC53-Cx21an3, aa 175 mutation, Arg to His) (26), human MDM2 (pCHDM1B) (27), and HM-Ub and HM-K48R-Ub (28) have been described. pCMV-GFP (Clontech) was used to express green fluorescent protein (GFP).

Cell Culture and Transfection. Saos-2, U2OS, SJSA-1 and NIH3T3 cells were obtained from the American Type Culture Collection (ATCC). Cells were cultured in DMEM (Saos-2, NIH3T3, p53−/− MEF, and p53−/− and MDM2−/− MEF; ref. (29) or RPMI(U2OS and SJSA-1) supplemented with 10% fetal bovine serum. Transfections were carried out using either Lipofectamine (Life Technologies) or FuGENE™6 (Roche) as described by the manufacturer.

Immunoprecipitation and Western blot analysis. Immunoprecipitation and Western blot analysis were performed as described (30). Cells were lysed with NP-40 lysis buffer on ice, and the protein extracts were precleared with prewashed Pierce Protein A/G agarose beads (50 µl of 50% slurry per 0.5 ml protein extract). The pre-cleared protein extracts were incubated with antibody for 8 hours to overnight at 4° C. on a rotating rocker, and then with the prewashed Pierce Protein A/G agarose beads for an additional 2 hours (10-15 µl of 50% slurry per 0.5 ml protein extract). The immunocomplex was washed 4 times with NP-40 buffer, dissolved in SDS loading buffer and fractionated on 10% SDS-polyacrylamide gels (BIO-RAD). The proteins were then transferred to NitroPure membrane (MSI) and incubated with specific antibody and appropriate horseradish-peroxidase-coupled secondary antibody (Santa Cruz and Promega). The membranes were washed in phosphate buffered saline (PBS) and visualized with ECL (Santa Cruz). Autoradiograms of Western blots were scanned with Scanmaster 3tm (Howtek) and analyzed using the Quantity One program (pdi). Antibodies used for immunoprecipations were rabbit anti-TSG101 (1:200, Clontech), anti-p53 (Ab-1, 1:400, Calbiochem), anti-MDM2 (SMP-14, 1:200, Santa Cruz Biotechnology), and anti-hemagglutinin (HA) (1:200, Clontech). Antibodies used for Western blots were rabbit anti-TSG101 (1:200, Clontech), anti-p53 (DO-1, 1:1000, Santa Cruz Biotechnology), anti-hemagglutinin (HA) (1:500, horseradish peroxidase (HRP)-labeled, Roche) and anti-Flag (1:500, M2, Kodak), anti-α-tubulin (1:20000, Neomark), anti-rabbit IgG (1:5000, HRP-labeled, Promega) and anti-mouse IgG (1:10,000, HRP-labeled, Santa Cruz Biotechnology). Anti-GFP antibody was obtained from Clontech and was used at 1:500 dilution.

in vivo Ubiquitination of MDM2. HM-Ub or HM-K48R-Ub was introduced into SJSA-1 cells by cotransfection with vectors expressing TSG101 mutant proteins B or F or with controls lacking an insert or expressing TSG101 cDNA in the antisense direction. Twenty-four hours later, the transfected cell cultures were treated with MG132 (2 µM) for 12 additional hours, lysed with 6 M guanidinium HCl, and sonicated for 20 s. The His-tagged proteins were purified using Ni-NTA spin columns (Qiagen), washed 4 times with 0.8 ml wash buffer (8 M Urea, 0.1 M NaH2PO4, 0.01 M Tris Cl, pH 6.2), and eluted once with wash buffer at pH 4, and an additional time with pH4 wash buffer containing 250 mM imidazole. The purified proteins were analyzed by Western blotting as above.

Pulse-Chase Experiments. NIH 3T3, p53$^{-/-}$ MEF, and p53$^{-/-}$/MDM2$^{-/-}$ MEF cells (1×10$^6$) were seeded onto 100 mm plates for 24 hours and were pulse-labeled with [$^{35}$S] methionine for 2 hours, washed twice with prewarmed PBS, and chased by culturing in DMEM supplemented with 10% fetal bovine serum for 0, 2, 4, 8, 12 hours. Cell lysates from pulse-labeled cells were immunoprecipitated with anti-TSG101 antibody (10 µg/500 µg total protein), resolved by electrophoresis in 10% SDS-polyacrylamide gels, and analyzed using a phosphoimager (ImageQuant Storm 840, Molecular Dynamics).

Results

Physical and functional interaction of TSG101 with p53 and MDM2. During investigations aimed at identifying physical and functional interactions between TSG101 and proteins previously implicated in tumorigenesis, we found that TSG101 can bind to both p53 and MDM2. This is shown in FIG. 1, which presents results of Western blot analyses of extracts of Saos-2 human osteosarcoma cells co-transfected with constructs expressing combinations of these proteins. Constructs expressing human TSG101, p53, or MDM2 proteins (2 µg of DNA for each plasmid) were introduced by transfection into Saos-2 cells, as indicated in Methods. Protein extracts from transfected cell populations were immunoprecipitated by the antibodies indicated. IP: immunoprecipitation, IB: immunoblotting. (a) Native or HA-tagged TSG101 or p53 proteins in Western blots were detected by anti-p53 monoclonal antibody (AB-1; 1:1000; the secondary antibody was goat anti-mouse HRP, diluted 1:1000) or (b) by anti-HA antibody labeled with HRP (diluted 1:500). (c) and (d) Western blot detection of immunoprecipitated proteins analyzed with anti-MDM2 antibody.

Complexes immunoprecipitated from cell extracts by antibody to TSG101 contained p53, either untagged or as fused to an influenza B hemagglutinin (HA) peptide epitope used for detection, and conversely, identified TSG101 in complexes immunoprecipitated with antibody to p53 (FIGS. 1a and b). Similarly, a 90 kD band detected with anti-MDM2 antibody and representing an MDM2 complex with the small ubiquitin-like protein, SUMO-1 (24) was present in Saos-2 cell protein complexes immunoprecipitated with antibodies to native or epitope-tagged TSG101 (FIGS. 1c and d).

Figure 2:
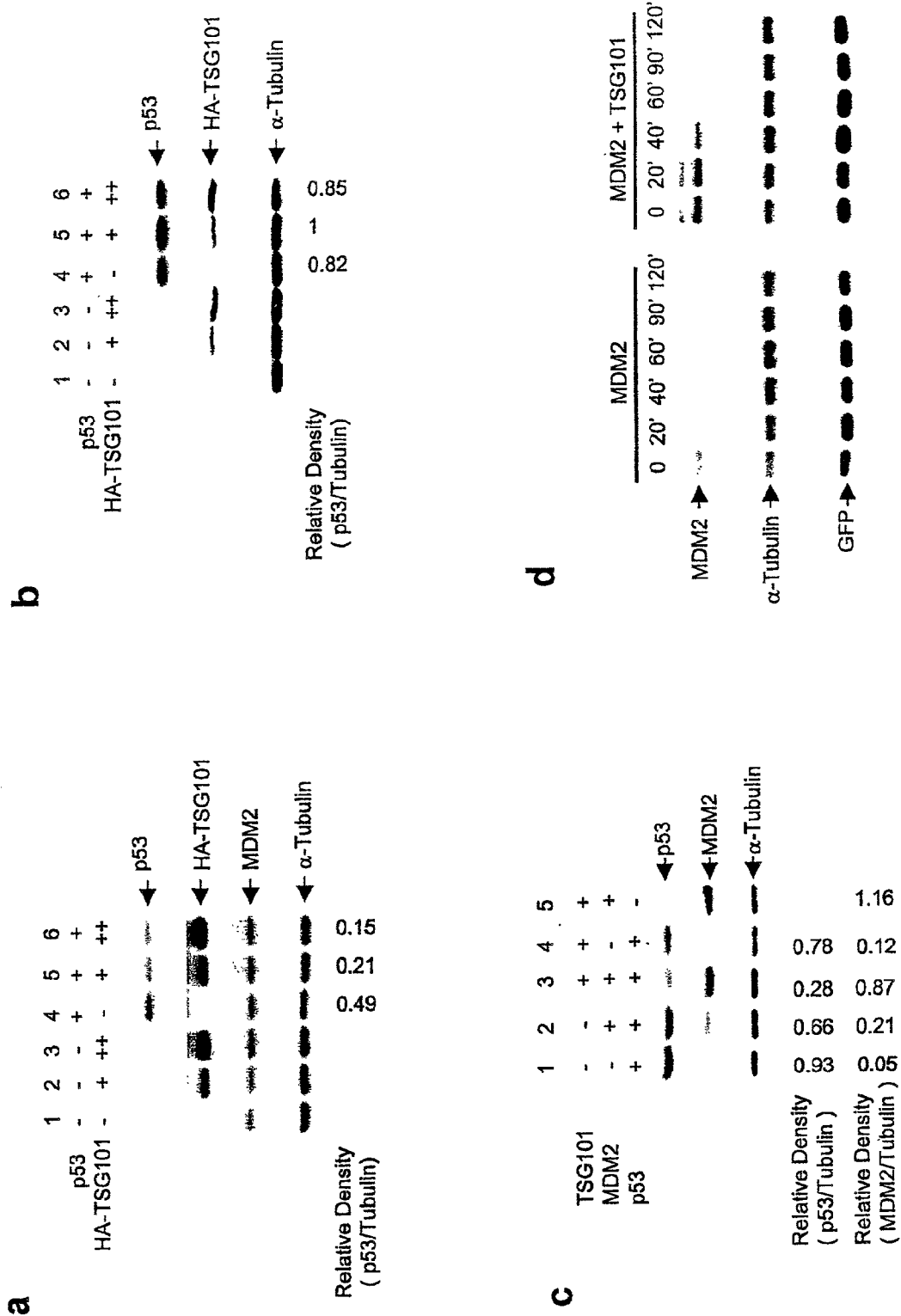
FIGS. 2A-E depict the results of experiments showing the effect of expression of TSG101 on the cellular level of p53 and the degradation of MDM2.

MDM2 is a ubiquitin protein ligase that mediates its own decay as well as the degradation of p53 (31, 32). That the ability of TSG101 to interact with MDM2 and/or p53 has functional consequences on the steady state levels of MDM2 and p53 is shown in FIG. 2: FIG. 2(a): The indicated constructs overexpressing p53 and HA-TSG101 were introduced into Saos-2 cells by transfection and p53 and HA-TSG101 levels were analyzed by Western blotting 48 hours later. + indicates 25 ng of transfected p53 expression vector DNA or 4 µg of HA-TSG101 expression vector DNA, ++ indicates 8 µg of HA-TSG101 expression vector DNA. The density of p53 bands relative to cellular α-tubulin was determined by scanning of exposed films. FIG. 2(b): The identical constructs overexpressing p53 and HA-TSG101 were introduced into p53$^{-/-}$/MDM2$^{-/-}$ MEF cells by transfection and p53 and HA-TSG101 levels were analyzed as in a.

TSG101 overexpression has divergent effects on the steady-state cellular levels of both the p53 and MDM2 proteins. As seen in FIG. 2a, overproduction of TSG101 in Saos-2 cells, which synthesize endogenous MDM2 protein but not native p53, reduced the level of p53 expressed from a transfected construct by 70%. However, in identically transfected cells that carry null chromosomal mutations in both p53 and MDM2 and thus lack the ability to synthesize either of these proteins [i.e., p53$^{-/-}$/MDM2$^{-/-}$ mouse embryo fibroblasts (MEF) (29, 33, 34); FIG. 2b], we observed no effect of TSG101 on p53—suggesting that TSG101-mediated reduction of the p53 level requires the presence of MDM2.

Although less than 50% of the population of Saos-2 cells was transfected by TSG101-expressing constructs under the experimental conditions we employed (data not shown), this was sufficient to elevate the MDM2 level in extracts of the entire cell population (FIG. 2a), supporting the notion that TSG101 down regulates p53 by elevating MDM2. Direct evidence for this conclusion was provided by experiments in which Saos-2 cells were transfected with constructs expressing p53, MDM2, and TSG101, individually or in combination. FIG. 2(c): Constructs overexpressing the proteins indicated were introduced into Saos-2 cells by transfection and p53 and MDM2 levels were analyzed as in a. + indicates 25 ng of transfected p53 expression vector DNA, 1 µg of MDM2 expression vector DNA, 4 µg of TSG101 expression vector DNA. Overproduction of MDM2 from a co-transfected CMV-based expression vector resulted in a decrease in the level of p53 protein (FIG. 2c, lanes 1-2); concurrent overproduction of TSG101 in co-transfected cells was associated with further elevation of the MDM2 protein level (FIG. 2c, lanes 3 and 5) and a prominent further decrease in p53 (lane 3).

Figure 2E:
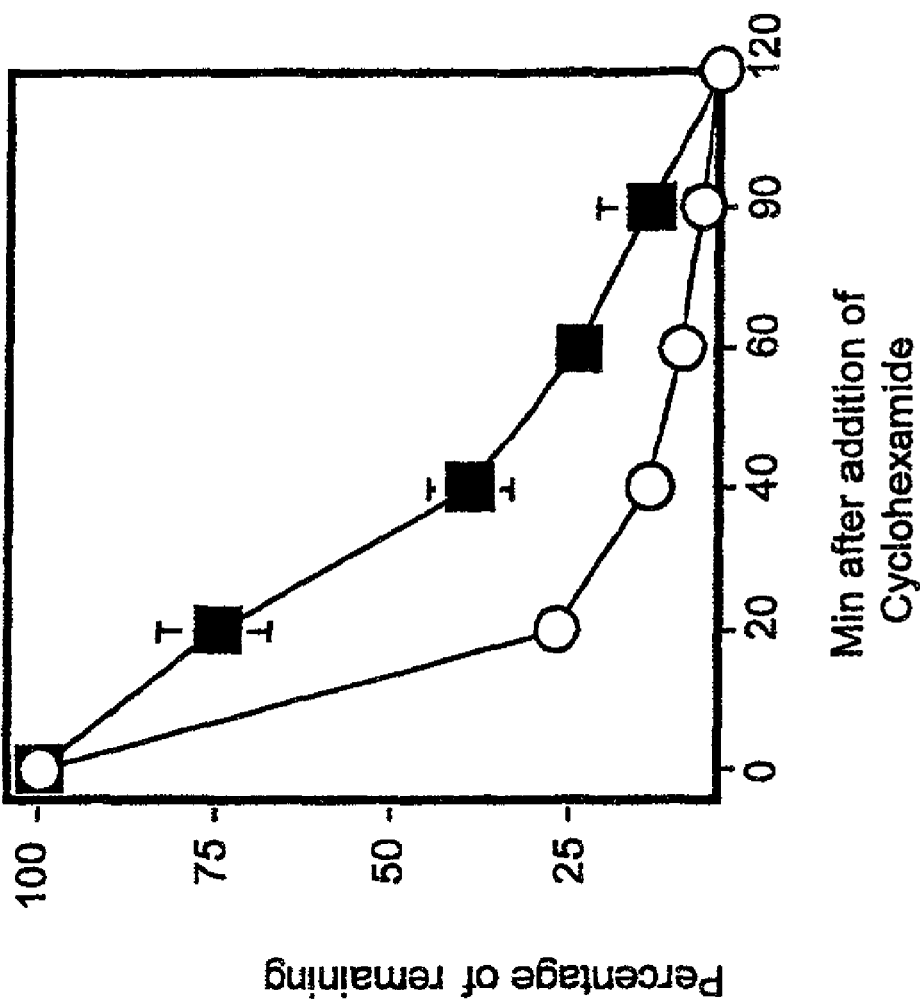

Effect of TSG101 on MDM2 decay. MDM2 normally has a short half-life of 15-20 minutes (35). FIG. 2(d): Saos-2 cells were transfected by an MDM2-expressing construct in the absence or presence of a TSG101-expressing construct. Cellular protein was extracted after addition of cyclohexamide at the indicated times and analyzed by Western blotting as in (a) using anti-MDM2 antibody. A GFP expression vector was co-transfected to normalize transfection efficiency; the expressed GFP protein was detected with anti-GFP antibody. FIG. 2(e): Plot of degradation of MDM2 for the experiment shown in (d), which was representative of five separate experiments. As seen in FIGS. 2d and e, TSG101 inhibits MDM2 degradation and prolongs its half-life. In this experiment, cells transfected with an construct expressing MDM2 from a CMV promoter, or co-transfected with constructs that express both MDM2 and TSG101, were treated with cyclohexamide to stop protein synthesis, and MDM2 protein was assayed by Western blot analysis of samples taken at the indicated times. The half-life observed for MDM2 (approximately 15 min), which is consistent with earlier determinations (35), nearly doubled (to 28 min) in cells that concurrently overexpressed TSG101.

The ubiquitin-conjugase-like Ubc domain of TSG101 inhibits ubiquitination of MDM2. Because the Ubc domain of TSG101 lacks a cysteine residue required for conjugase function (12-14), it previously was speculated that TSG101 may inhibit ubiquitination by forming non-productive complexes with ubiquitin or its target proteins and consequently interfering with the function of bona fide E2 (12, 13). The results seen in FIG. 3a, which show the effects of mutant TSG101 proteins on the steady state level of MDM2 expressed from a co-transfected construct, indicate that TSG101's ability to stabilize MDM2 is sharply reduced by deletion of sequences from the Ubc domain. They also show that overexpression of the TSG101 Ubc domain's 'a' region, which contains residues bracketing the 'active site' locus that in functional E2 enzymes contains a cystein, is sufficient to cause accumulation of MDM2 (construct A). The presence of the 'b' region of TSG101's Ubc domain enhanced the effects of the 'a' region and even in the absence of $Ubc_a$ led to some stabilization of MDM2 (constructs B vs. A and E vs. F).

Figure 3:
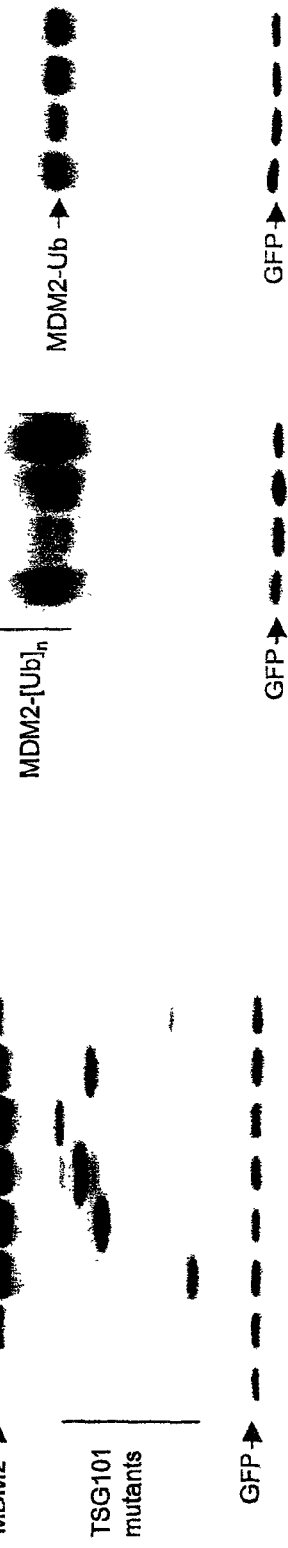
FIGS. 3A and 3B depict the results of experiments showing the effects of Ubc domains of TSG101 on MDM2 degradation and ubiquitination.

Further analysis of truncated TSG101 proteins consisting of largely the Ubc domain (construct TSB101B) or lacking this domain (construct TSG101F) showed that overexpression of the TSG101 Ubc domain interferes with ubiquitination of endogenous MDM2 (FIG. 3b). In the experiment shown in the left panel, cellular proteins conjugated to His-tagged ubiquitin were isolated by Ni-NTA column chromatography, and MDM2 was identified in this protein pool by Western blotting using anti-MDM2 antibody. Notwithstanding the ability of TSG101 and its Ubc domain to globally increase the cellular level of both endogenous and adventitious MDM2 (FIG. 2), cells overproducing the TSG101 Ubc domain showed a decrease in ubiquitinated MDM2 vs. controls (FIG. 3b left panel, lanes 1 and 2). That the TSG101 Ubc domain can decrease ubiquitination of MDM2 was demonstrated also by an experiment in which ubiquitin chains initiated on cellular proteins were tagged with a Ub variant (K48R) (28) that impedes ubiquitin chain elongation; this preserves tagged proteins and allows the extent of Ub addition to endogenous MDM2 to be evaluated by immunoprecipitation of MDM2 (FIG. 3b, right panel).

FIG. 3(a) The indicated constructs expressing c-Myc tagged full-length and deletion mutants of TSG101 (A-F, 8 µg), a construct expressing HA-tagged MDM2 (1.5 µg), and a construct expressing GFP (2 ng) were introduced into U2OS cells by transfection. HA-MDM2, c-Myc tagged TSG101s (A-F) and GFP were detected by Western blotting 48 hours after transfection with anti-HA, anti-c-Myc and anti-GFP antibodies. (b) The indicated constructs express ubiquitin tagged with both $His_6$ and c-Myc (HM-Ub, 5 µg, left panel), or a dominant negative variant ubiquitin tagged with $His_6$ and c-Myc (HM-K48R-Ub, 5 µg, right panel). These were co-transfected into SJSA-1 cells with a GFP expression and construct (2 ng), constructs expressing TSG101 mutant B or F (4 µg each), a construct expressing antisense TSG101 (4 µg), or a construct containing no DNA insert (4 µg). Protein extracts were applied to Ni-NTA columns and the ubiquitin labeled MDM2 was eluted and detected by Western blotting with anti-MDM2 antibody. 1/20 of protein extracts was used for the detection of GFP by Western blot to normalize for transfection efficiency.

MDM2 modulates the decay of TSG101. Earlier work has shown that both TSG101 excess and deficiency can lead to abnormal cell growth (1) and that the steady state level of TSG101 protein normally is regulated within a narrow range by proteolysis (3). Just as TSG101 modulates the MDM2 level by negatively regulating its ubiquitination and decay, we found that MDM2 has a parallel key role in the proteolysis of TSG101. This action of MDM2 was suggested initially by the observation that the intracellular concentration of endogenous TSG101 relative to α-tubulin was markedly higher in $p53^{-/-}/MDM2^{-/-}$ MEFs than in $p53^{-/-}$ MEF cells, which are capable of producing MDM2 (FIG. 4a). The correctness of the notion that MDM2, which as already noted mediates the degradation of both itself and p53, also affects the decay of TSG101 was supported by multiple lines of evidence. Firstly, the pulse-chase experiment seen in FIG. 4b shows that the decay of endogenous TSG101 was accelerated in $p53^{-/-}$ MEFs but was reduced in MEFs doubly mutated in p53 and MDM2. Secondly, SJSA-1 cells, which contain multiple copies of MDM2 as a result of gene amplification (16), showed a major deficiency of endogenous TSG101, as compared with cells (U2OS and Saos-2) containing a single chromosomal copy of MDM2 (FIG. 4c). Thirdly, a dosage dependent decrease of Flag-tagged TSG101 protein expressed from the CVM promoter was observed in Saos-2 cells co-transfected with constructs that produce adventitious MDM2 (FIG. 4d); because Saos-2 cells lack p53, this experiment also indicates that MDM2 mediated acceleration of TSG101 decay does not require p53. Finally, while p53 overexpression, which activates endogenous MDM2 production (1, 16), was associated with a decrease in TSG101, overexpression of a mutant p53 protein that lacks the ability to increase endogenous MDM2 had no effect on the TSG101 level (FIG. 4e).

That the effects of MDM2 on TSG101 degradation are, like those of p53, carried out by the 26S proteasome was shown by an experiment in which addition of the proteasome inhibitor, MG132, resulted in accumulation of endogenous TSG101 (FIG. 4f). Moreover, in the presence of MG132, overexpression of MDM2—which accumulated to >40× normal levels when the proteasome inhibitor was present—failed to accelerate decay of TSG101, confirming that MDM2-promoted decay of TSG101 requires proteasome action (FIG. 4g).

Figure 4:
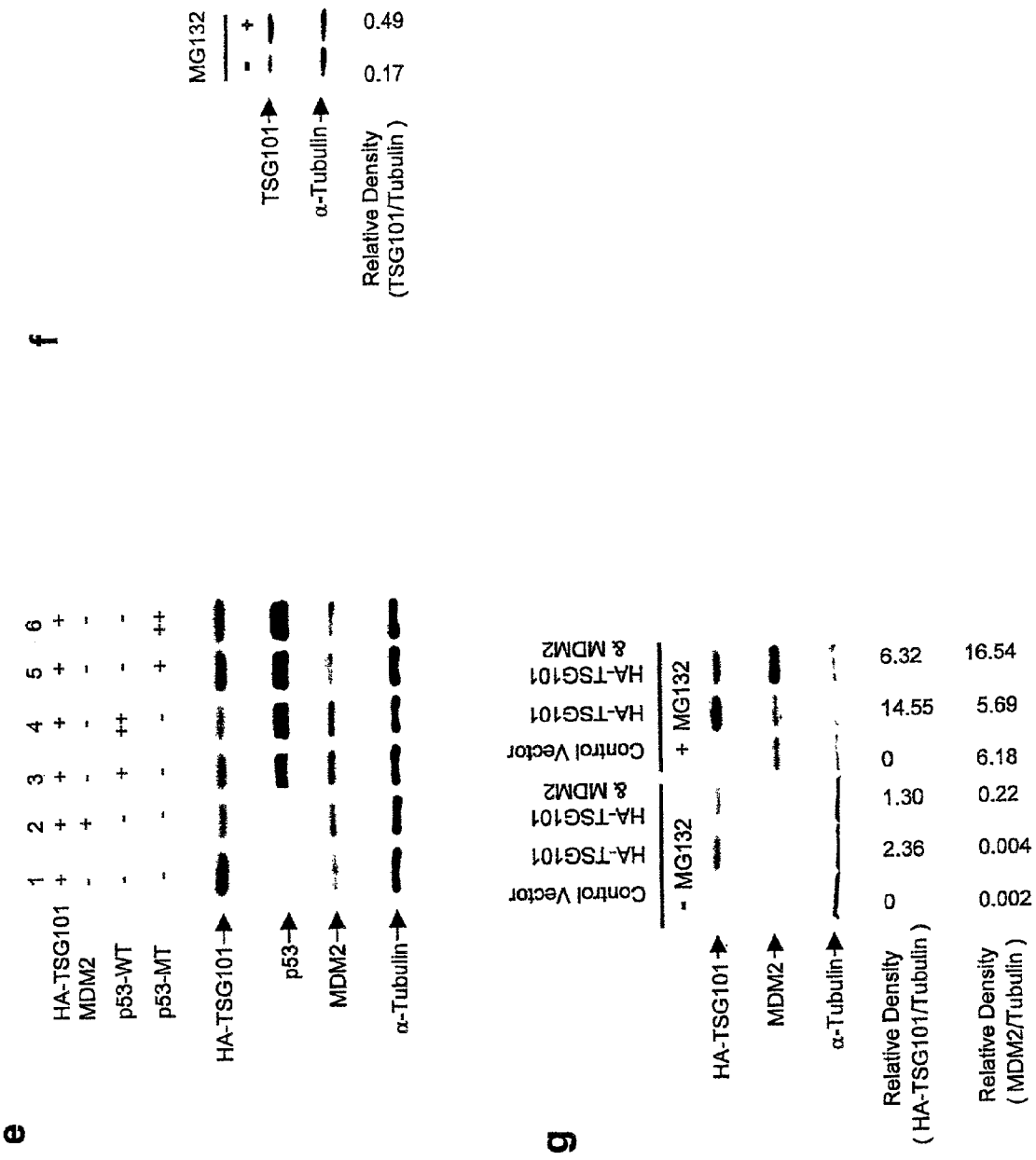
FIGS. 4A-4G depict the results of experiments showing MDM2-dependent proteolysis of TSG101.
Figure 5:
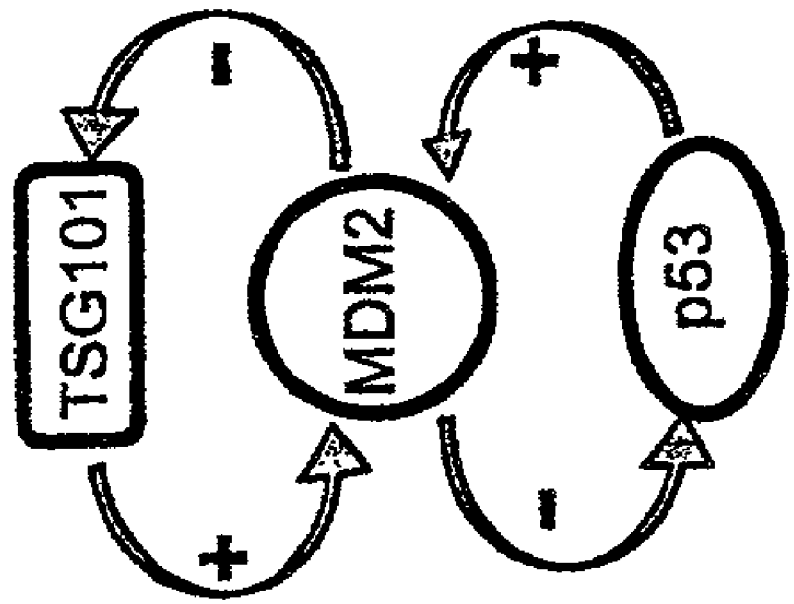
FIG. 5 depicts a model showing functional interactions of the TSG101/MDM2 and p53/MDM2 feedback control loops.

FIG. 4. (a) Cellular TSG101 protein levels detected by Western blotting with protein extracts (40 μg each) from mouse fibroblast NIH 3T3 cells, p53$^{-/-}$ mouse embryo fibroblasts (MEF), and mouse embryo fibroblasts mutated in both p53 and MDM2. Relative densities of TSG101 protein bands were calculated after normalization to cellular α-tubulin. (b) Cell cultures of NIH 3T3, p53$^{-/-}$ MEF and p53$^{-/-}$/MDM2$^{-/-}$ MEF were pulse labeled with $^{35}$S-methionine for 1 hour, and chased for 0, 2, 4, 8 and 12 hours. The $^{35}$S-labeled TSG101 was immunoprecipitated by anti-TSG101 antibody, resolved in SDS gel, and visualized and quantitated by ImageQuant. (c) Vectors expressing Flag-tagged TSG101 and MDM2 were introduced into Saos-2 cells by co-transfection. Transfecting amounts of DNA are designated by + for 0.5 μg Flag-TSG101 expression vector and + to ++++ for 1 to 4 μg MDM2 expression vector. (d) Combinations of vectors expressing MDM2, HA-tagged TSG101, and/or mutant or wild type p53 protein were introduced by transfection into Saos-2 cells and protein extracts of transfectants were analyzed by Western blotting using antibody as indicated. Where indicated, transfectants received 1 μg plasmid DNA expressing HA-TSG101, 1 μg plasmid DNA expressing MDM2, and p53-expressing constructs as follows: + and ++, 1 μg and 2 μg respectively. The p53 mutation replaced the Arg at aa 175 with His. (e) Saos-2 cell cultures were treated as indicated with MG132 (2 μM) for 24 hours and cellular protein extracts were analyzed by Western blotting with anti-TSG101 antibody. (f) Protein extracts from SJSA-1, U2OS, and Saos-2 cells were analyzed by Western blot using antibodies to MDM2, p53, TSG101 and α-tubulin. The ratio of MDM2/TSG101 was determined after normalization with cellular α-tubulin. The indicated constructs were introduced into Saos-2 cells by transfection (concentrations designated as in FIG. 4d). Transfected cells were cultured in the absence or presence of MG132 for 24 hours and protein extracts of cells were analyzed by Western blotting with anti-HA and anti-MDM2 antibody. The intensity of HA-TSG101 and MDM2 protein bands is indicated relative to cellular α-tubulin.

REFERENCES

1. Li, L. & Cohen, S. N. (1996) *Cell* 85, 319-29.
2. Xie, W., Li, L. & Cohen, S. N. (1998) *Proc Natl Acad Sci USA* 95, 1595-600.
3. Feng, G. H., Lih, C. J. & Cohen, S. N. (2000) *Cancer Res* 60, 1736-41.
4. Gayther, S. A., Barski, P., Batley, S. J., Li, L., de Foy, K. A., Cohen, S. N., Ponder, B. A. & Caldas, C. (1997) *Oncogene* 15, 2119-26.
5. Turpin, E., Dalle, B., de Roquancourt, A., Plassa, L. F., Marty, M., Janin, A., Beuzard, Y. & de The, H. (1999) *Oncogene* 18, 7834-7.
6. Lee, M. P. & Feinberg, A. P. (1997) *Cancer Res* 57, 3131-4.
7. Sun, Z., Pan, J., Bubley, G. & Balk, S. P. (1997) *Oncogene* 15, 3121-5.
8. Wagner, K. U., Dierisseau, P., Rucker, E. B., 3rd, Robinson, G. W. & Hennighausen, L. (1998) *Oncogene* 17, 2761-70.
9. Watanabe, M., Yanagi, Y., Masuhiro, Y., Yano, T., Yoshikawa, H., Yanagisawa, J. & Kato, S. (1998) *Biochem Biophys Res Commun* 245, 900-5.
10. Sun, Z., Pan, J., Hope, W. X., Cohen, S. N. & Balk, S. P. (1999) *Cancer* 86, 689-96.
11. Hittelman, A. B., Burakov, D., Iniguez-Lluhi, J. A., Freedman, L. P. & Garabedian, M. J. (1999) *Embo J* 18, 5380-8.
12. Koonin, E. V. & Abagyan, R. A. (1997) *Nat Genet* 16, 330-1.
13. Ponting, C. P., Cai, Y. D. & Bork, P. (1997) *J Mol Med* 75, 467-9.
14. Hochstrasser, M. (2000) *Science* 289, 563-4.
15. Levine, A. J. (1997) *Cell* 88, 323-31.
16. Freedman, D. A. & Levine, A. J. (1999) *Cancer Res* 59, 1-7.
17. Prives, C. (1998) *Cell* 95, 5-8.
18. Oren, M. (1999) *J Biol Chem* 274, 36031-4.
19. Lane, D. P. & Hall, P. A. (1997) *Trends Biochem Sci* 22, 372-4.
20. Haupt, Y., Maya, R., Kazaz, A. & Oren, M. (1997) *Nature* 387, 296-9.
21. Kubbutat, M. H., Jones, S. N. & Vousden, K. H. (1997) *Nature* 387, 299-303.
22. Zhang, Y., Xiong, Y. & Yarbrough, W. G. (1998) *Cell* 92, 725-34.
23. Sherr, C. J. & Weber, J. D. (2000) *Curr Opin Genet Dev* 10, 94-9.
24. Buschmann, T., Fuchs, S. Y., Lee, C. G., Pan, Z. Q. & Ronai, Z. (2000) *Cell* 101, 753-62.
25. Baker, S. J., Markowitz, S., Fearon, E. R., Willson, J. K. & Vogelstein, B. (1990) *Science* 249, 912-5.
26. Levine, A. J., Wu, M. C., Chang, A., Silver, A., Attiyeh, E. F., Lin, J. & Epstein, C. B. (1995) *Ann N Y Acad Sci* 768, 111-28.
27. Chen, J., Marechal, V. & Levine, A. J. (1993) *Mol Cell Biol* 13, 4107-14.
28. Ward, C. L., Omura, S. & Kopito, R. R. (1995) *Cell* 83, 121-7.
29. McMasters, K. M., Montes de Oca Luna, R., Pena, J. R. & Lozano, G. (1996) *Oncogene* 13, 1731-6.
30. Fiddler, T. A., Smith, L., Tapscott, S. J. & Thayer, M. J. (1996) *Mol Cell Biol* 16, 5048-57.
31. Honda, R. & Yasuda, H. (1999) *Embo J* 18, 22-7.
32. Fang, S., Jensen, J. P., Ludwig, R. L., Vousden, K. H. & Weissman, A. M. (2000) *J Biol Chem* 275, 8945-51.
33. Montes de Oca Luna, R., Wagner, D. S. & Lozano, G. (1995) *Nature* 378, 203-6.
34. Jones, S. N., Roe, A. E., Donehower, L. A. & Bradley, A. (1995) *Nature* 378, 206-8.
35. Olson, D. C., Marechal, V., Momand, J., Chen, J., Romocki, C. & Levine, A. J. (1993) *Oncogene* 8, 2353-60.
36. Vousden, K. H. (2000) *Cell* 103, 691-4.
37. Roth, J., Dobbelstein, M., Freedman, D. A., Shenk, T. & Levine, A. J. (1998) *Embo J* 17, 554-64.
38. Ruland, J., Sirard, C., Elia, A., MacPherson, D., Wakeham, A., Li, L., de la Pompa, J. L., Cohen, S. N. & Mak, T. W. (2001) *Proc Natl Acad Sci USA*, 98 1859-64.
39. Hsieh, J. K., Chan, F. S., O'Connor, D. J., Mittnacht, S., Zhong, S. & Lu, X. (1999) *Mol Cell* 3, 181-93.
40. VanDemark et al., (2001), *Cell* 105, 711-720.
41. Weissman (2001) *Nature Reviews* 2, 169-178.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention.

Various references are cited herein, each of which is incorporated-by-reference herein in its entirety for all purposes. Such references include but are not limited to Li et al., (2001) *Proc Natl Acad Sci USA* 98, 1619-1624.

What is claimed is:

1. An isolated monoclonal antibody that binds specifically to a polypeptide comprising a ubiquitination-regulating domain, or a functional fragment thereof, of a human TSG101 protein comprising the amino acid sequence of SEQ ID NO: 1, wherein said antibody binds specifically to said ubiquitination-regulating domain; and
   wherein said antibody binds specifically to an epitope in the ubiquitination-regulating domain of TSG101 protein found in amino acid residues 1-250 of SEQ NO: 1 and by so binding, said antibody modulates interaction between said human TSG101 protein thereof and MDM2 protein.

2. An isolated monoclonal antibody that binds specifically to a polypeptide comprising a ubiquitination-regulating domain, of a human TSG101 protein comprising the amino acid sequence of SEQ ID NO: 1, wherein said antibody binds specifically to said ubiquitination-regulating domain; and
   wherein said antibody binds specifically to an epitope in the ubiquitination-regulating domain of TSG101 protein found in amino acid residues, wherein said ubiquitination-regulating domain comprises amino acid residues 50-140 of SEQ ID NO:1, and wherein said epitope is found in amino acid residues 50-140 of SEQ ID NO:1.

3. An isolated monoclonal antibody that binds specifically to a polypeptide comprising a ubiquitination-regulating domain, or a functional fragment thereof, of a human TSG101 protein comprising the amino acid sequence of SEQ ID NO: 1, wherein said antibody binds specifically to said ubiquitination-regulating domain; and
   wherein said antibody binds specifically to an epitope in the ubiquitination-regulating domain of TSG101 protein found in amino acid residues 1-140 of SEQ ID NO: 1, and wherein said epitope is found in amino acid residues 1-140 of SEQ ID NO:1.

4. The antibody of claim 1, wherein said ubiquitination-regulating domain comprises amino acid residues 140-250 of SEQ ID NO: 1, and wherein said epitope is found in amino acid residues 140-250 of SEQ ID NO:1.

5. A pharmaceutical composition for treatment of diseases involving TSG101-mediated ubiquitination, comprising:
   an isolated monoclonal antibody that binds specifically to a polypeptide comprising an ubiquitination-regulating domain, of a human TSG101 protein comprising the amino acid sequence of SEQ ID NO:1, wherein said antibody binds specifically to said ubiquitination-regulating domain,
wherein said antibody binds specifically to an epitope in the ubiquitination regulating domain of TSG101 protein found in amino acid residues 1-250 of SEQ ID NO: 1, and
a pharmaceutically acceptable excipient.

6. A method for treatment of diseases involving TSG101-mediated ubiquitination, said method comprising:
administering to a subject suffering from a disease involving TSG101-mediated ubiquitination an effective amount of the pharmaceutical composition of claim 5.

7. The method of claim 6, wherein the diseases involving TSG101-mediated ubiquitination comprise proliferative diseases, neurodegenerative diseases, autoimmune diseases, and developmental abnormalities.

8. An isolated monoclonal antibody that binds specifically to a ubiquitination-regulating domain of TSG101, wherein said domain consists of amino acid residues 1-250 of SEQ ID NO: 1, and
wherein said antibody specifically binds to an epitope in the ubiquitination regulating domain of TSG101 protein found in amino acid residues 1-250 of SEQ ID NO: 1 and by so binding, said antibody modulates interaction between said human TSG101 protein or functional fragment thereof and MDM2 protein.

9. The isolated antibody of claim 8, wherein said ubiquitination-regulating domain consists of amino acid residues 50-140 of SEQ ID NO: 1, or a functional fragment thereof, and wherein said epitope is found in amino acid residues 50-140 of SEQ ID NO:1.

10. The isolated antibody of claim 8, wherein said ubiquitination-regulating domain consists of amino acid residues 1-140 of SEQ ID NO: 1, or a functional fragment thereof, and wherein said epitope is found in amino acid residues 1-140 of SEQ ID NO:1.

11. The isolated antibody of claim 8, wherein said ubiquitination regulating domain consists of amino acid residues 140-250 of SEQ ID NO: 1, or a functional fragment thereof, and wherein said epitope is found in amino acid residues 140-250 of SEQ ID NO:1.

12. A pharmaceutical composition for treatment of diseases involving TSG101-mediated ubiquitination, comprising:
an isolated monoclonal antibody that binds specifically to a ubiquitination-regulating domain of human TSG101, wherein said antibody binds specifically to an epitope in the ubiquitination-regulating domain of TSG101 protein found in amino acids 1-250 of SEQ ID NO: 1; and, a pharmaceutically acceptable excipient, wherein said pharmaceutically acceptable excipient is acceptable for administration to a mammal.

13. The pharmaceutical composition of claim 12, wherein, when administered to a mammal in an amount effective for the purpose, said antibody modulates interaction between TSG101 protein and MDM2 protein in said mammal.

* * * * *

UNITED STATES PATENT AND TRADEMARK OFFICE
CERTIFICATE OF CORRECTION

| | | |
|---|---|---|
| PATENT NO. | : 7,714,108 B2 | Page 1 of 1 |
| APPLICATION NO. | : 10/053975 | |
| DATED | : May 11, 2010 | |
| INVENTOR(S) | : Li et al. | |

It is certified that error appears in the above-identified patent and that said Letters Patent is hereby corrected as shown below:

Col. 1 line 11, please insert:

-- FEDERALLY-SPONSORED RESEARCH OR DEVELOPMENT

This invention was made with Government support under contract HG000325 awarded by the National Institutes of Health. The Government has certain rights in this invention. --

Signed and Sealed this
Ninth Day of August, 2011

David J. Kappos
*Director of the United States Patent and Trademark Office*